United States Patent
Leblans et al.

(10) Patent No.: US 9,326,741 B2
(45) Date of Patent: May 3, 2016

(54) STORAGE SCREENS FOR MEDICAL RADIOGRAPHY

(75) Inventors: Paul Leblans, Kontich (BE); Jean-Pierre Tahon, Langdorp (BE)

(73) Assignee: Agfa Healthcare NV, Mortsel (BE)

( * ) Notice: Subject to any disclaimer, the term of this patent is extended or adjusted under 35 U.S.C. 154(b) by 177 days.

(21) Appl. No.: 14/117,333

(22) PCT Filed: May 23, 2012

(86) PCT No.: PCT/EP2012/059559
§ 371 (c)(1),
(2), (4) Date: Nov. 12, 2013

(87) PCT Pub. No.: WO2012/160079
PCT Pub. Date: Nov. 29, 2012

(65) Prior Publication Data
US 2014/0186657 A1    Jul. 3, 2014

(30) Foreign Application Priority Data
May 24, 2011    (BE) .................................. 2011/0318

(51) Int. Cl.
*A61B 6/00*    (2006.01)
*G21K 4/00*    (2006.01)

(52) U.S. Cl.
CPC ................ *A61B 6/4216* (2013.01); *G21K 4/00* (2013.01)

(58) Field of Classification Search
CPC ........................................................ A61L 2/04
See application file for complete search history.

(56) References Cited

U.S. PATENT DOCUMENTS

2008/0085228 A1*    4/2008    Yamazaki et al. ............ 422/291

FOREIGN PATENT DOCUMENTS

| EP | 0234385 A1 | 9/1987 |
| EP | 0835920 A1 | 4/1998 |
| WO | WO 2009/144982 A1 | 12/2009 |

OTHER PUBLICATIONS

International Search Report in corresponding International Patent Application No. PCT/EP2012/059559, mailed Jul. 4, 2012.
Kalathingal, Sajitha, et al., "An evaluation of microbiologic contamination on a phosphor plate system: is weekly gas sterilization enough?," *Oral Surgery, Oral Medicine, Oral Pathology, Oral Radiology, and Endodontology*, vol. 109, pp. 457-462 (2010).

\* cited by examiner

*Primary Examiner* — Nathan T Leong
(74) *Attorney, Agent, or Firm* — Leydig, Voit & Mayer, Ltd.

(57) ABSTRACT

The present invention concerns a method for the treatment of stimulable phosphors and/or screens for use in diagnosis, in particular medical radiography. The method comprises subjecting the stimulable phosphors and/or screens to an epoxide containing gaseous compound, promptly following their manufacture. By applying the method according to the invention yellowing of the stimulable phosphors and/or screens is prevented in a safe and efficient manner; thereby the disadvantages known as such resulting from such yellowing will not occur.

9 Claims, No Drawings

STORAGE SCREENS FOR MEDICAL RADIOGRAPHY

CROSS-REFERENCE TO RELATED APPLICATIONS

This patent application is a U.S. National Phase Patent Application of International Patent Application No. PCT/EP2012/059559, filed May 23, 2012, which claims the benefit of Belgian Patent Application No. 2011/0318, filed May 24, 2011, both of which are incorporated by reference in their entireties.

FIELD OF THE INVENTION

The present invention relates to a method for the production of phosphor storage screens for use in diagnosis, more in particular for use in medical radiography. The treatment of screens according to the present invention takes place during and after the production of such screens. According to the method of the invention the so-produced screens are treated with an epoxides compound such as oxirane so as to prevent yellowing of the screens in a later stage, and the problems related with such yellowing.

The method according to the invention is likewise applicable to semi-finished products in the production of screens as well as to phosphors for use in such screens.

BACKGROUND OF THE INVENTION

It is common knowledge that nowadays needle phosphors as well as powder phosphors are used in the production of storage phosphors screens for computed radiography.

In the case of powder phosphors use is often made of divalent europium activated alkaline earth metal fluoro-halide phosphors. Barium-fluoro-bromide/iodide compounds are commonly used. Storage phosphors used in such screens can have, for e.g. the following composition $Ba_{0.928}Sr_{0.07}Eu_{0.002}F_{1.05}Br_{0.80}I_{0.15}$. In the case of powder phosphor screens, these compounds are coated as powders in a layer on a support.

Generally, a barium-fluoro-bromide (BaFBrI) phosphor is coated onto a support, e.g. made of polyester. In particular, a support made of polyethylene terephthalate (PET) with a thickness of approximately 250μ is often used as support. Such support is usually supplied in the form of a roll. This roll is de-rolled and a phosphor composition is then coated on the support. After, the coated support is dried and a protective layer is coated on the dried phosphor layer. The finished layers are then slit and cut to the usual commercial dimensions of phosphor screens.

Such commercially usual formats depend on the envisaged application; when referring to medical diagnosis applications, general radiography, mammography or dental applications are usually included. Apart from medical diagnosis, non-destructive testing of materials is another field of application where such screens may also be used.

In contrast to said powder phosphor screens, in the case of needle phosphor screens, the phosphor layer is formed on the surface of a carrier or support, made for e.g. aluminum, in the form of needles through a vapour deposition technique. In the later case, cesium-bromide compounds are often used.

In the case of phosphor screens using phosphor powder compounds incorporating iodine, in the course of its use, a yellowing of the screens occur.

A drawback occasioned by such yellowing is that such screen is characterized by an unpleasing appearance for the user; it also gives to said screen a weary appearance. A further and more technical disadvantage is that when the screen is read out in a digitizer, an uneven or stained image is detected. This is the main disadvantage, since it compromises use of the plate for (medical) diagnosis.

The probable cause of this phenomenon is that iodine, present for e.g. 15 mol %, is available for oxidation at the surface of the grain and as a result is converted to iodine gas. This oxidation is catalysed by ultraviolet (UV) irradiation, humidity and acid atmospheric conditions (pH<7). The vapour pressure of the so formed iodine gas is low, and as a result it remains in the phosphor screen and does not, or only very partially, escapes from said screen.

The visual result is a noticeable yellowing of the screen. As such, this phenomenon does not adversely affect the functioning of the phosphor during a radiographic exposure. The screen stores the radiographic 'latent' image just like before the yellowing phenomenon. However, during the subsequent phase, i.e. is during the reading out of the phosphor screen by the digitizer, the formed iodine will partly absorb the blue emission light of the phosphor. As a result, these yellow stains will also become visual on the digitally read-out image as stained areas with a lower signal strength. This is clearly unacceptable since the quality of the medical diagnosis is negatively influenced by this event.

Iodide ($I^-$) is far easier oxidized compared to bromide ($Br^-$) and certainly compared to fluoride ($F^-$). For the later two ions the problem as described above does not occur when storage phosphor screens are used in conformity with usual working conditions.

The yellowing problem of the phosphor screens and the resulting local weakening of the emission light occurs not only in the case of phosphor screens used for general radiography (e.g. for exposure of the lungs or the thorax) but for special radiographic applications such as mammography as well. In case of using said phosphor screens for non-destructive testing this is also a disadvantage. However, this situation is a major issue when such phosphor screens are meant to be used in dental applications.

The reason for the latter phenomenon is as follows: storage phosphor screens for general or mammography applications are usually stored in a cassette and thus they are shielded from light. In contrary, usually storage screens for dental applications are neither stored in a cassette nor in a transparent housing. Therefore, no shield from light is provided in such cases.

Typically, storage screens for dental applications are for each new exposure put in a new plastic envelope. After exposure, the phosphor screen is taken out of the respective envelope for being read out. Then, if the phosphor screen is intended to be used again it is placed in a new envelope. In between such uses this phosphor screen is exposed to UV light and air humidity.

Epoxide-containing compounds are known for long. In particular, oxirane (ethyleneoxide) is well known for application in sterilisation of objects.

The general chemical formula of oxirane is $C_2H_4O_2$ and the structural formula is as follows:

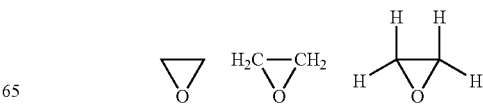

Treating objects with oxirane is a method known as such but only aiming sterilisation. This method is used for e.g. in hospital environment for the sterilisation of drapes, gowns and surgical instruments generally.

There are also publications that describe the sterilization stimulable of phosphor screens by using this method. An example of such publication is the article "An evaluation of microbiologic contamination on a phosphor plate system: is weekly gas sterilization enough?" Oral Surg. Oral Med. Oral Pathol. Oral Radiol. Endod. 2010; 109: 457-462. This article describes how microbiological contamination of photostimulable phosphor screen is countered by gas-sterilization using ethylene-oxide.

To this end, each Friday all phosphor screens are sterilized by using a model 4XL Steri-Vac gas sterilization chamber, produced by 3M Health Care, St. Paul, Minn., USA.

A similar publication is the US2008/0085228 A1. This document describes how a digitizer for stimulable phosphor screens (a so-called digitizer) comprises a sterilization or disinfection unit that applies a sterilization or disinfection treatment to a photostimulable phosphor screen. As disinfectant treatment various possibilities are described, including a gas-treatment. The use of ethylene oxide as gas for such purpose is disclosed.

The aim of the later two disclosures however is quite distinct from the aim of the present invention since only disinfection of the phosphor screens is intended. Besides, the treatment herein described is superficial and takes place at a time that the yellowing problem has already occurred and cannot be solved any more. In fact, as soon as the gaseous iodide has been formed in the phosphor layer, the yellowing problem occurs and cannot be remedied any more by a later superficial treatment of the phosphor layer.

From document EP 0 234 385 the yellowing problem of phosphor screens is well known. The solution disclosed herein comprises the addition of a compound having an epoxy group to the phosphor screen. In particular, whenever said phosphor screen comprises an iodine phosphor composition, such as a divalent europium activated alkaline earth metal fluoro-halide phosphor. This compound may be added to the layer containing the phosphor. In this case, the epoxy containing compound can also act as binder for the phosphor. In an alternate arrangement, such compound may be added to a neighbouring layer of the phosphor layer.

According to this disclosure, these compounds are proposed to be added as liquid epoxides to the phosphor layer composition; throughout the specification disclosure is made of polymer coatings, but also the 1,2 epoxypropane compound is mentioned ($C_3H_6O$). This method however has many drawbacks:

Most of the examples cited in the text are directed to a resin, which reactivity is inherently limited. The reason for that is because resin molecules are by definition long molecules and thus less mobile, or have a limited diffusion velocity. This resin with reduced mobility must bridge the distance to the phosphor particle. However, in quite a number of cases this is impossible because the phosphor layer quickly dries after coating. Therefore, the resin molecules are in fact immobilised in the phosphor layer and as a result of this they become useless for the aim as set forth above. This phenomenon and resulting disadvantage is even stronger when the resin molecules are present in a layer neighbouring the phosphor layer instead of being present in the phosphor layer itself.

One should also take into account the thickness of the phosphor layer; In the case of general medical radiographic applications, such thickness is of approximately 250µ, in mammographic applications it is of approximately 150µ, whereas in the case of dental applications it is even less thick, of approximately 100µ.

Should the molecular weight of the epoxy-containing compounds decreases the above mentioned disadvantages also decrease. However, in this case another drawback arises, namely the evaporation of low-molecular weight epoxy containing compounds during the coating- and drying operations of the phosphor layer. Because of the evaporation such compounds do not have the time, and consequently the opportunity, to react with the iodine compounds at the surface of the phosphor particles.

As result, the gain occasioned by the use of more reactive low-molecular weight compounds is lost through the loss of such compounds of the phosphor mixture, due to the evaporation of such compounds from the coated phosphor layer.

The practical result of this is that the still present reactive iodide at the surface of the phosphor particle after coating and drying of the phosphor layer, cannot be 'treated' by the still present immobile epoxides in such layer. Eventually, this gives raise to yellowing phenomenon of the screens causing the problems as described above.

A second disadvantage of this method is that the presence of such extra component reduces the packing density of the phosphor screen; this packing density should be as high as possible in case of stimulable phosphor screens.

A third disadvantage of this method is that the presence of such extra component negatively influences the drying characteristics of the phosphor layer in production. This, in turn leads to screen structure and variations in packing density. Such kind of variations in the packing density is of primary concern in the production of powder phosphor screens.

Finally, there is still another important disadvantage linked to method disclosed in EP 0 234 385: working with such resins, which comprise toxic components raise a number of issues in practical working conditions, ex. from the point of view of safety of the installations, such as increasing the risk of explosion and, from the point of view of the operating staff increased health risk due to carcinogenic components. Moreover, the end product, the stimulable phosphor screen still contains a certain amount of such compounds.

For all of the above mentioned reasons the need to develop a production method devoid of many or all of the above mentioned problems still remains.

SUMMARY OF THE INVENTION

It is an object of the present invention to provide a method for producing and treating storage phosphorus screens for radiography that allow to solve the above mentioned drawbacks in an efficient and simple manner. In particular, it is proposed a method for producing and treating phosphor screens having iodine in their composition that prevents the yellowing of said screens.

This object is realised by providing a phosphor screen and a method for producing phosphorous screens as defined herein.

Further advantages and embodiments of the present invention will become apparent from the following description.

DETAILED DESCRIPTION OF THE INVENTION

The present invention relates to a method for producing and treating a storage phosphorus screen for radiography wherein said phosphorous screen comprises a phosphorous composition containing iodine and wherein a treatment with at least an epoxy group containing compound in gaseous form is applied to said phosphorous composition.

It is believed that the treatment of phosphor screens with at least a compound comprising at least an epoxy group results in a nucleophylic substitution by the strongly nucleophylic iodide on the epoxy compound.

Because a phosphor layer upon coating and drying can contain up to 30% by volume of air, the epoxy compound molecules can relatively easily enter such porous phosphor screens and exert its function. In the case of oxirane, it is thought that probably the triangle opens up and interacts with the surface of the phosphor particle. Probably the following compound is formed: $I-(CH_2-CH_2-O-)_n-H$ with $n \geq 0$.

As mentioned before, typically a barium-fluoro-bromide (BaFBrI) phosphor is coated onto a support, e.g. made of polyester. In particular, a support made of polyethylene terephthalate (PET) with a thickness of approximately 250μ is often used. Such support is usually supplied in the form of a roll. This roll is de-rolled and a phosphor composition is then coated on the support. After, the coated support is dried and a protective layer is coated on the dried phosphor layer. The finished layers are then slit and cut to the usual commercial dimensions of phosphor screens.

According to one embodiment of the present invention, the above described production method of phosphor screens can continue to be used in unaltered form and mode since it is sufficient to apply the treatment with at least one epoxy group containing compound to the phosphor screens manufactured as described above, to solve the problems and drawbacks previously mentioned.

In this sense, phosphor screens produced as e.g. according to the method described above are placed in an after-treatment room, an autoclave or sterilisation room. In this isolated environment they are put into contact with gaseous epoxide-containing compounds like e.g. oxirane. The phosphor screens, after their manufacture, are introduced in a sterilisation chamber or room, wherein they are contacted during a predefined amount of time with a gaseous epoxide-containing compound. In a particularly preferred embodiment of the present invention, oxirane or ethylene-oxide is the epoxy group containing compound used.

The method according to the present invention should take place during or after the production of the phosphor screens. The phosphor screens produced, and even after being on roll again, are placed in an autoclave, and subjected to the oxirane treatment. Therefore, the final production step of the phosphor screens can occur, i.e. the slitting and cutting of the phosphor screens on roll unto the commercially usual formats.

According to another embodiment of the present invention, a so called pre-slitting of the phosphor screen rolls takes place into strips, whereupon these strips are subjected to the oxirane treatment. After this treatment according to the invention, the final slitting and cutting of the phosphor screens takes place to yield the commercially usual formats of the screens.

Another embodiment of the present invention is that the final slitting and cutting of the phosphor screen rolls takes place before the treatment according to the invention. In the latter case, the slit and cut phosphor screens are subjected to the epoxide treatment.

The invention as above described is applied preferably on phosphor screens, after their production but before their being put on the market.

However, the method of the present invention can also be applied to semi-finished products, i.e. in the production of the phosphor screens, as well as on the powder phosphors itself for use in such screens.

For this purpose, the treatment with at least an epoxy group containing compound in gaseous form can be applied to the selected phosphor composition during the manufacturing process of the phosphor screen, i.e. before said composition is applied onto the substrate.

In alternative, the treatment with at least an epoxy group containing compound in gaseous form can be applied to the phosphor composition after said composition is applied to the substrate and before the phosphor screen is finished.

In conclusion, the method of the present invention is useful to produce phosphor screens comprising a phosphor composition that includes iodine wherein at least an epoxy group containing compound in gaseous form can be applicable either to finished phosphor screens or during the production of said screens, namely to the phosphor composition comprising iodine before its application onto the substrate or after its application onto the substrate.

The invention claimed is:

1. A method for the production of a phosphorous screen wherein
   i) said phosphorous screen comprises a phosphorous composition containing iodine, and
   ii) a treatment with at least an epoxy group containing compound in gaseous form is applied to the phosphorous composition of i) during the manufacturing process of the phosphorous screen, wherein
   iii) the treatment of ii) is applied in an after-treatment room, autoclave or sterilization room.

2. The method according to claim 1, wherein the phosphorous composition comprises alkaline earth material halogenide phosphors.

3. The method according to claim 1, wherein the phosphorous composition further comprises a bariumfluorohalogenide phosphor.

4. The method according to claim 1, wherein the phosphorous composition also comprises divalent europium as activator.

5. The method according to claim 1, wherein the epoxy group containing compound is oxirane.

6. The method according to claim 1, wherein the treatment with at least an epoxy group containing compound is performed to the phosphorous composition before it is applied onto the screen.

7. The method according to claim 1, wherein the treatment with at least an epoxy group containing compound is performed to the phosphorous composition after said composition is applied to the screen and before the screen is slit and/or cut into desirable formats and shapes.

8. The method according to claim 7, wherin the phosphorous screen is slit and/or cut into the desirable formats and shapes after the treatment with at least an epoxy group containing compound is performed to the phosphorous composition.

9. The method according to claim 7, wherein the phosphorous composition is a powder.

* * * * *